(12) United States Patent
Wagner

(10) Patent No.: US 9,130,172 B2
(45) Date of Patent: Sep. 8, 2015

(54) NAPHTHYL-CONTAINING COMPOUNDS FOR LIGHT-EMITTING DEVICES

(71) Applicant: Carl Wagner, Glendale, AZ (US)

(72) Inventor: Carl Wagner, Glendale, AZ (US)

(73) Assignee: Arizona Board of Regents, a body corporate of the State of Arizona acting for and on behalf of Arizona State University, Scottsdale, AZ (US)

( * ) Notice: Subject to any disclaimer, the term of this patent is extended or adjusted under 35 U.S.C. 154(b) by 0 days.

(21) Appl. No.: 14/399,620

(22) PCT Filed: May 8, 2013

(86) PCT No.: PCT/US2013/040168
§ 371 (c)(1),
(2) Date: Nov. 7, 2014

(87) PCT Pub. No.: WO2013/169918
PCT Pub. Date: Nov. 14, 2013

(65) Prior Publication Data
US 2015/0119582 A1 Apr. 30, 2015

Related U.S. Application Data

(60) Provisional application No. 61/644,092, filed on May 8, 2012.

(51) Int. Cl.
| | |
|---|---|
| C07C 211/58 | (2006.01) |
| H01L 51/00 | (2006.01) |
| C09K 11/06 | (2006.01) |
| H01L 51/50 | (2006.01) |
| C07D 333/20 | (2006.01) |
| H01L 27/32 | (2006.01) |

(52) U.S. Cl.
CPC ............ *H01L 51/006* (2013.01); *C07C 211/58* (2013.01); *C07D 333/20* (2013.01); *C09K 11/06* (2013.01); *H01L 27/3241* (2013.01); *H01L 51/0068* (2013.01); *H01L 51/5012* (2013.01); *H01L 51/5056* (2013.01); *C09K 2211/1007* (2013.01); *C09K 2211/1011* (2013.01); *C09K 2211/1014* (2013.01); *C09K 2211/1092* (2013.01); *H01L 51/0058* (2013.01)

(58) Field of Classification Search
CPC .................................................. H01L 51/006
USPC ........................................................ 549/74
See application file for complete search history.

(56) References Cited

U.S. PATENT DOCUMENTS

| | | | |
|---|---|---|---|
| 2005/0280008 A1* | 12/2005 | Ricks et al. ...................... 257/79 |
| 2010/0096982 A1* | 4/2010 | Eum et al. ...................... 313/504 |

FOREIGN PATENT DOCUMENTS

| | | | |
|---|---|---|---|
| CN | 1807396 | * | 7/2006 |
| CN | 101540375 A | | 9/2009 |
| EP | 2103666 A3 | | 4/2010 |
| JP | 2005112765 | * | 4/2005 |
| JP | 2005112765 A | | 4/2005 |
| JP | 2008311480 | * | 12/2008 |
| KR | 2008096440 | * | 10/2008 |
| WO | WO2007061218 | * | 5/2007 |
| WO | WO2011041529 A3 | | 8/2011 |
| WO | WO2013169918 A1 | | 11/2013 |

OTHER PUBLICATIONS

King, Med. Chem., Principle and Practice (1994), pp. 206-208.*
PCT Officer Tai Hyun Kang, International Search Report and Written Opinion of International Application No. PCT/US2013/040168, mailed Aug. 6, 2013, 9 pages.
Carl E. Wagner et al., "Synthesis of Tri-2-Naphthylamine and Related Compounds Via the Buchwald-Hartwig Amination," 2009, 9 pages.
Jwo-Huei Jou et al., "Nanodot-Enhanced High-Efficiency Pure-White Organic Light-Emitting Diodes with Mixed-Host Structures," Advanced Functional Materials, vol. 18, Issue 1, Jan. 2008, pp. 121-126.
Jwo-Huei Jou, "Hole-transporting-layer-free high-efficiency fluorescent blue organic light-emitting diodes," Applied Physics Letters, vol. 91, Jul. 2007, pp. 043504-1-043504-3.
Dong-Ha Kim et al., "New Host Materials Containing Carbazole and Naphthyl Moieties for Green Dopant in Phosphorescence Organic Light-Emitting Diodes (OLEDs)," Bulletin of the Korean Chemical Society, vol. 29, Issue 11, 2008, pp. 2270-2272.
S.C. Tse et al., "Single-layer organic light-emitting diodes using naphthyl diamine," Applied Physics Letters, vol. 91, May 2007, pp. 213502-1-213502-3.
Yunxia Guan et al., "White organic light-emitting diodes with 9, 10-bis (2-naphthyl) anthracene," Journal of Physics: Conference Series, vol. 152, No. 1, Mar. 2009, 5 pages.
PCT Officer Simin Baharlou, International Preliminary Report on Patentability of International Application No. PCT/US2013/040168, mailed Nov. 20, 2014, 6 pages.

* cited by examiner

*Primary Examiner* — Taofiq A Solola
(74) *Attorney, Agent, or Firm* — Fish & Richardson P.C.

(57) ABSTRACT

Naphthyl-containing compounds having structural formula $S_2R$ for use in organic light-emitting diodes (OLEDs). R may include an aromatic group, a heterocyclic group, or a group that is both aromatic and heterocyclic. In some examples, R is phenyl, biphenyl, and thiophenyl. OLEDs including these compounds are shown to emit in a range between 400 nm and 700 nm. These OLEDs are suitable for devices including televisions, laptop computers, computer monitors, personal digital assistants, mobile phones, portable media players, watches, test devices, advertising displays, information displays, indication displays, and large-area light-emitting elements for general illumination.

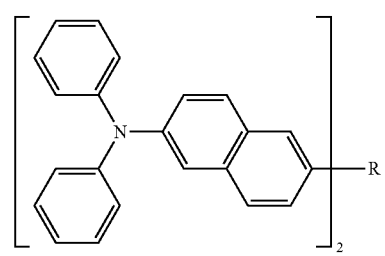

8 Claims, 14 Drawing Sheets

NAPHTHYL-CONTAINING COMPOUNDS FOR LIGHT-EMITTING DEVICES

CROSS-REFERENCE TO RELATED APPLICATIONS

This application is a U.S. National Phase Application of International Patent Application No. PCT/US2013/040168 filed May 8, 2013, which claims the benefit of U.S. Provisional Application Ser. No. 61/644,092 filed on May 8, 2012, the contents of both of which are incorporated herein by reference in their entirety.

TECHNICAL FIELD

This disclosure is related to naphthyl-containing compounds, organic light-emitting diodes (OLEDs) including the naphthyl-containing compounds, and devices including the OLEDs.

BACKGROUND

FIG. 1A depicts organic light-emitting device (OLED) 100, which includes substrate 102 with a layer of indium tin oxide as an anode 104, a layer of hole-transporting materials (HTL) 106, a layer of light processing material 108, such as emissive materials (EML) including emitter and host for an OLED, a layer of electron-transporting materials (ETL) 110, and a metal cathode layer 112. The emission color of an OLED is determined by the emission energy (optical energy gap) of the light processing material 108. Naphthyl-containing materials have been used as blue light emitters in OLED emissive layers. Devices such as televisions, laptop computers, computer monitors, personal digital assistants, mobile phones, portable media players, watches, test devices, displays (e.g., for advertising, information, and indication), or large-area light-emitting elements for general illumination may include one or more OLEDs. FIG. 1B depicts device 120 including a multiplicity of OLEDs 100.

SUMMARY

A first general aspect includes naphthyl-containing compounds having structural formula $S_2R$:

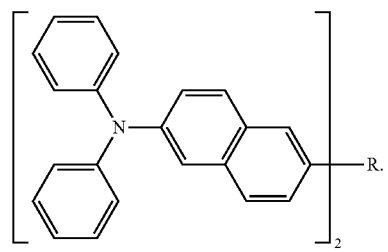

These napthyl-containing compounds may be used in organic light-emitting diodes (OLEDs).

In some implementations, R is an aromatic group, a heterocyclic group, or a group that is both aromatic and heterocylic. In certain implementations, R is phenyl, biphenyl, or thiophenyl.

In some implementations, $S_2R$ has the skeleton:

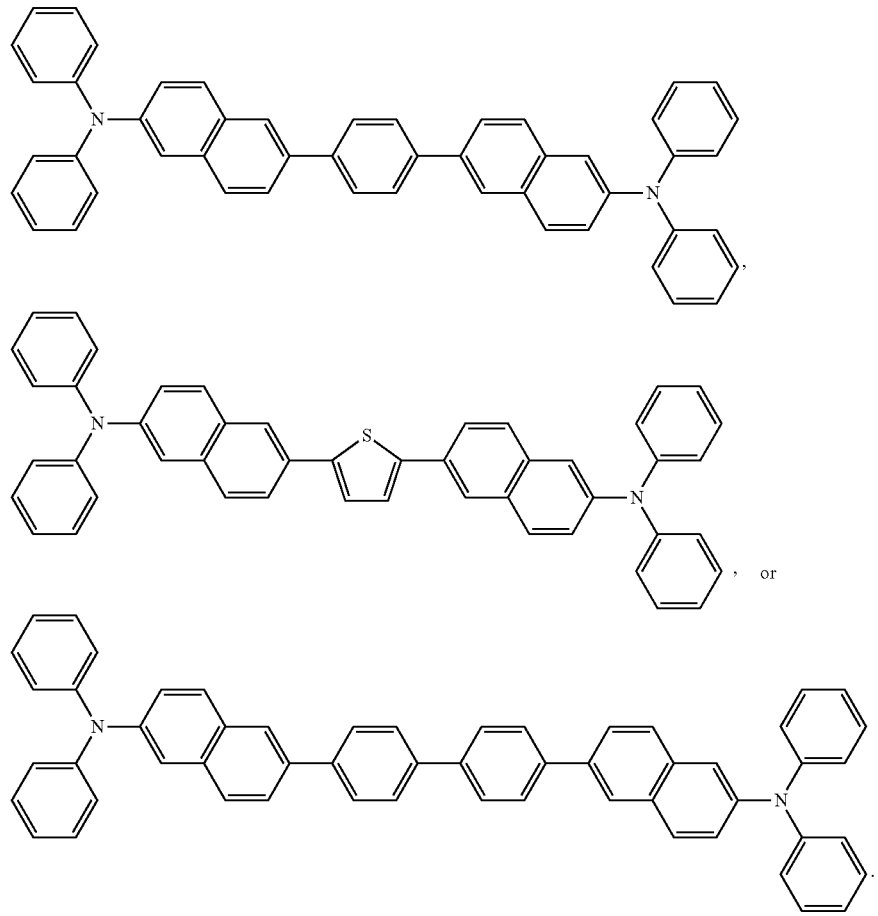

A second general aspect includes OLEDs including naphthyl-containing compounds described herein.

A third general aspect includes devices including OLEDs of the second general aspect. Such devices may include, for example, televisions, laptop computers, computer monitors, personal digital assistants, mobile phones, portable media players, watches, test devices, advertising displays, information displays, indication displays, and large-area light-emitting elements for general illumination.

These general and specific aspects may be implemented using a device, system or method, or any combination of devices, systems, or methods. The details of one or more embodiments are set forth in the accompanying drawings and the description below. Other features, objects, and advantages will be apparent from the description and drawings, and from the claims.

BRIEF DESCRIPTION OF THE DRAWINGS

The concepts herein may be more completely understood in consideration of the following detailed description of various embodiments in connection with the accompanying drawings.

DETAILED DESCRIPTION

Figure 1A:
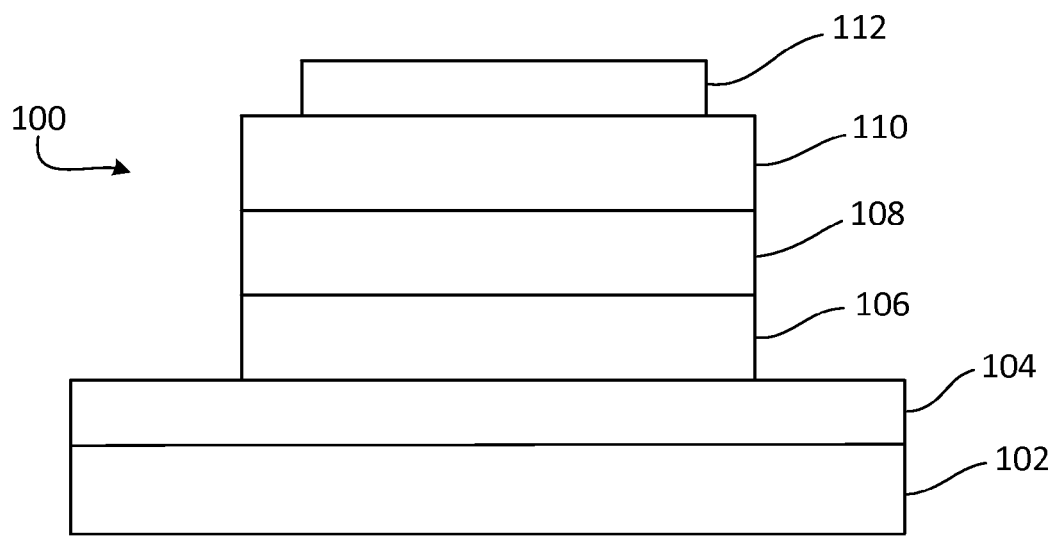
FIG. 1A depicts an organic light-emitting device (OLED).
Figure 1B:
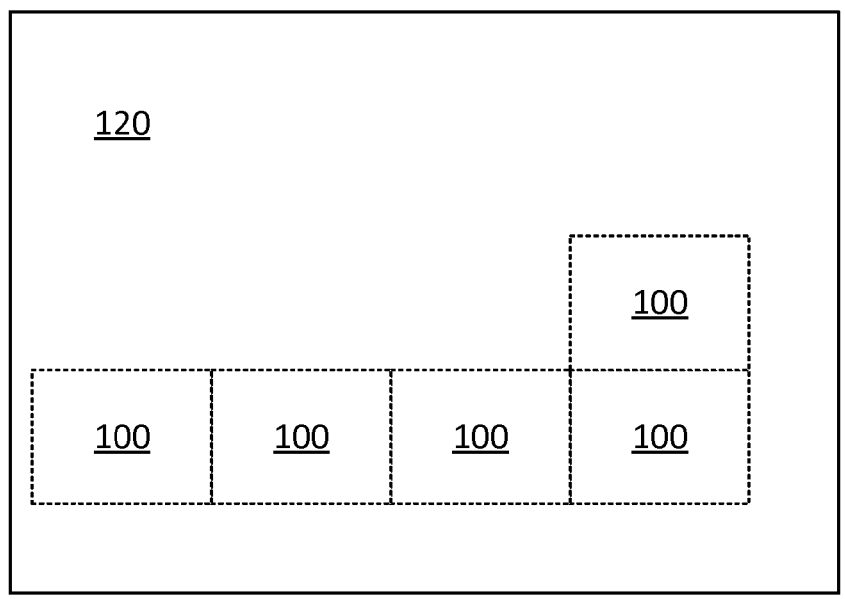
FIG. 1B depicts a device including an OLED.

Naphthyl-containing compounds described herein can be depicted as $S_2R$, where S is

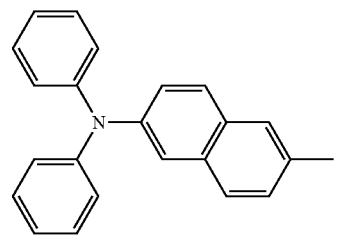 [SMILES: Cc1ccc2cc(N(c3ccccc3)c3ccccc3)ccc2c1]

and $S_2R$ is

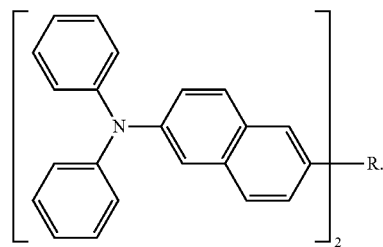

S and R may be substituted or unsubstituted. R may be a heterocyclic or a carbocyclic group, and may be an alkyl group or an aryl group, including a fused aryl group. In some examples, R is phenyl, biphenyl, thiophenyl, and the like. These napthyl-containing compounds may be used as emissive materials in OLEDS.

Examples of napthyl-containing compounds include compounds having skeletons such as Structural Formula 1, Structural Formula 2, and Structural Formula 3, shown below.

Structural Formula 1

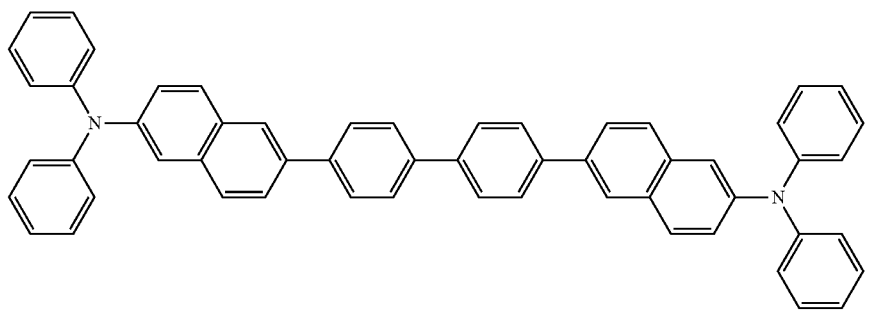

Structural Formula 2

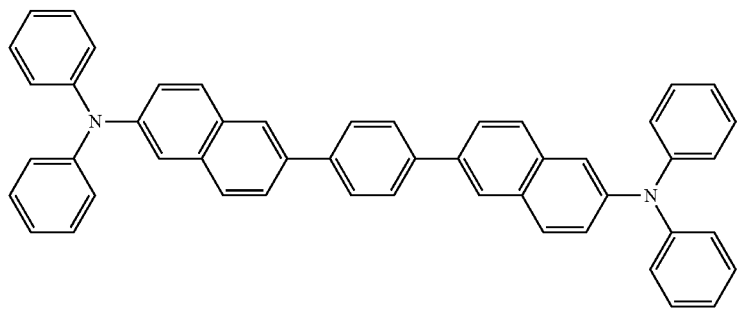

Structural Formula 3

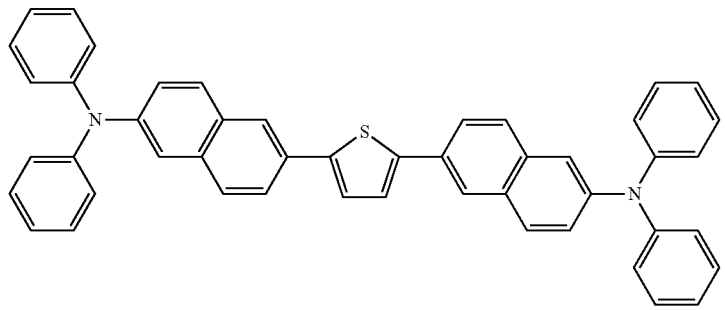

Compounds described herein, such as Structural Formulas 1-3, may be substituted or unsubstituted, and may be synthesized following Suzuki reaction coupling conditions as described below.

Compound 1.

6-(4-(2-(diphenylamino)naphthalen-6-yl)-4'-biphenyl)-N,N-diphenylnaphthalen-2-amine, shown below, was synthesized in the following manner.

Compound 1

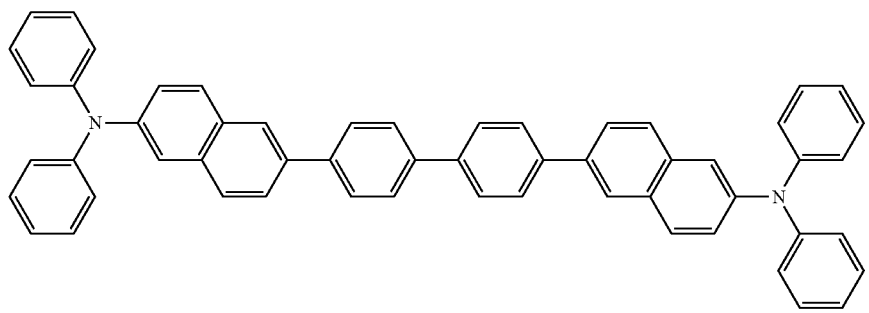

To a solution of 6-bromo-N,N-diphenylnaphthalen-2-amine (1.0028 g, 2.65 mmols), 4,4'-diphenyldiboronic acid (0.3188 g, 1.32 mmols), sodium carbonate (0.87 g, 8 mmols), and TBAB (0.856 g) in water (6.1 mL) was added Pd(OAc)$_2$ (0.035 g, 0.03 mmols). The solution was degassed with nitrogen, and heated to 155° C. for 5 min. The reaction solution was then poured into ethyl acetate and water. A precipitate was filtered off and redissolved in hot toluene, and the organic layer was concentrated, and the crude product was chromatographed (2.5-100% ethyl acetate in hexanes, and then hot toluene, silica gel) to give the title compound (0.200 g, 20%) as a yellow, crystalline compound: $^1$H NMR (400 MHz, CDCl$_3$) δ 8.03 (s, 2H), 7.77-7.83 (m, 10H), 7.74 (d, J=8.8, 2.0 Hz, 2H), 7.68 (d, J=8.4 Hz, 2H), 7.46 (d, J=2.0 Hz, 2H), 7.33 (dd, J=9.2, 2.4 Hz, 2H), 7.29 (t, J=7.6 Hz, 8H), 7.17 (d, J=8.4 Hz, 8H), 7.07 (t, J=8.4 Hz, 4H); $^{13}$C NMR (100 MHz, CDCl$_3$) δ 147.6, 145.6, 140.0, 139.4, 136.5, 133.6, 130.1, 129.3, 129.1, 127.6, 127.5, 127.4, 125.7, 125.3, 124.7, 124.4, 123.0, 119.6; LCMS (M+H)$^+$ Calc'd for C$_{56}$H$_{41}$N$_2$ 741.3269. found 741.3270.

Absorption spectra were measured on a Shimadzu UV-3101PC UV-vis-NIR spectrometer. Absorption spectra for Compounds 1, 2, and 3 were taken in dichloromethane.

Steady-state fluorescence spectra were measured using a Photon Technology International MP-1 spectrometer and corrected for detection system response. Excitation was provided by a 75 W xenon-arc lamp and single grating monochromator. Fluorescence was detected 90° to the excitation beam via a single grating monochromator and an R928 photomultiplier tube having S-20 spectral response and operating in the single photon counting mode.

Figure 2A:
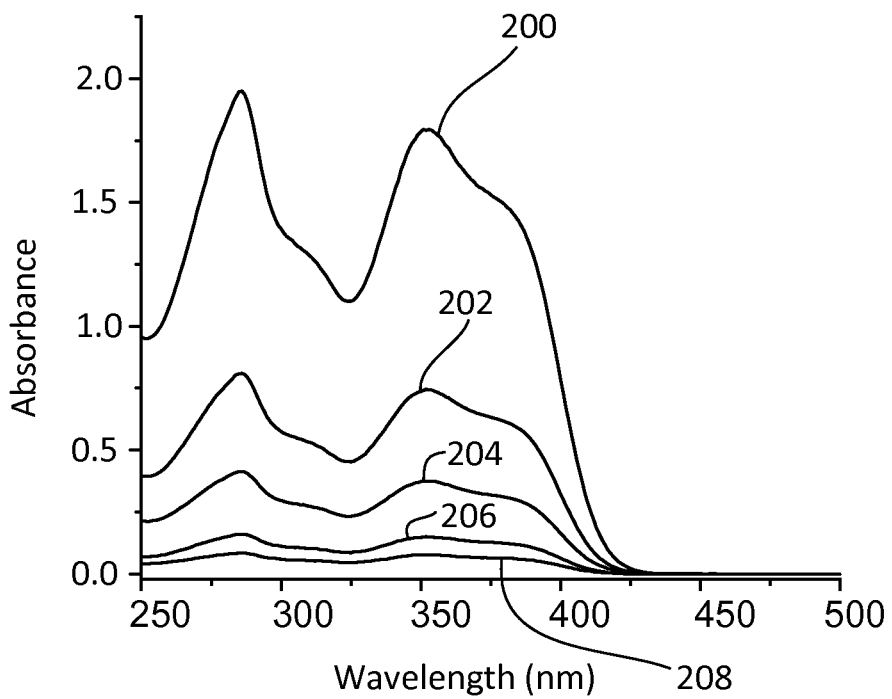
FIG. 2A depicts UV-vis spectra of 6-(4-(2-(diphenylamino)naphthalen-6-yl)-4'-biphenyl)-N,N-diphenylnaphthalen-2-amine (Compound 1).

FIG. 2A shows UV-vis spectra of Compound 1 synthesized as described above, with plots 200, 202, 204, 206, and 208 corresponding to concentrations of 2.81×10$^{-5}$M, 1.12×10$^{-5}$ M, 5.61×10$^{-6}$M, 2.25×10$^{-6}$M, and 1.12×10$^{-6}$M, respectively, in dichloromethane. The absorbance maximum ($\lambda_{Max,Abs}$) emission maximum ($\lambda_{Max,Em}$), and extinction coefficient (ε) are shown in Table I.

TABLE I

Properties of Compounds 1-3.

| | $\lambda_{Max\,Abs}$ (nm) | $\epsilon$ ($M^{-1} \cdot cm^{-1}$) | $\lambda_{Max\,Em}$ (nm) | Φ | $E_{HOMO}$ (eV)[c] | E° (V)[a] |
|---|---|---|---|---|---|---|
| Compound 1 | 286 | 69,000 | 286 | — | −5.24 | 0.46 |
| | 352 | 64,000 | | | | (72)[b] |
| Compound 2 | 283 | 64,000 | 283 | — | −5.26 | 0.48 |
| | 352 | 57,000 | | | | (59)[b] |
| | | | | | | 1.41* |
| Compound 3 | 289 | 53,000 | 410 | — | −5.15 | 0.38 |
| | 410 | 61,000 | | | | (90)[b] |
| NPD[d] | — | — | — | — | −5.30 | 0.38 |

[a] Versus Fe/Fe⁺.

*Indicates irreversible oxidation whose $E_{ox}$ is $E_p$.

[b] The peak-to-peak separation (mV) listed in parentheses for redox processes exhibiting reversible electrode kinetics.

[c] D'Andrade, B.W.; Datta, S.; Forrest, S.R.; Djurovich, P.; Polikarpov, E.; Thompson, M.E., *Organic Electronics* 2005, 6, 11-20.

[d] Estimated.

In Table I, NPD refers to N,N-di(naphthalene-1-yl)-N,N'-diphenyl-benzidine, shown below.

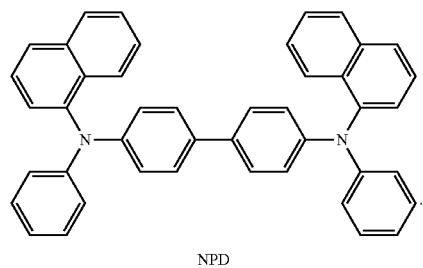 [SMILES: c1ccc(N(c2ccc(-c3ccc(N(c4ccccc4)c4cccc5ccccc45)cc3)cc2)c2cccc3ccccc23)cc1 ; "NPD"]

NPD

Cyclic voltammetry was performed with a CHI 650C potentiostat (CH Instruments) using a glassy carbon disk (3 mm) working electrode, a Pt gauze counter electrode, and a silver wire pseudo-reference electrode in a conventional three-electrode cell. These measurements were carried out in anhydrous dichloromethane (freshly distilled from calcium hydride), deoxygenated by bubbling with argon, with 0.10 M tetrabutylammonium hexafluorophosphate as the supporting electrolyte. The working electrode was cleaned between experiments by polishing with a 0.05 μm alumina slurry, followed by solvent rinses. The concentration of the electroactive compound was maintained between $1.9 \times 10^{-4}$ M and $2.0 \times 10^{-4}$ M. After each voltammetric experiment, ferrocene was added to the solution, and the potential axis was calibrated against the formal potential of the ferrocenium/ferrocene redox couple (taken as 0.45 V vs SCE in dichloromethane). The data presented in Table I ($E_{HOMO}$ and E°) is for voltammograms recorded at 35, 50, and 100 mV s⁻¹.

Figure 2B:
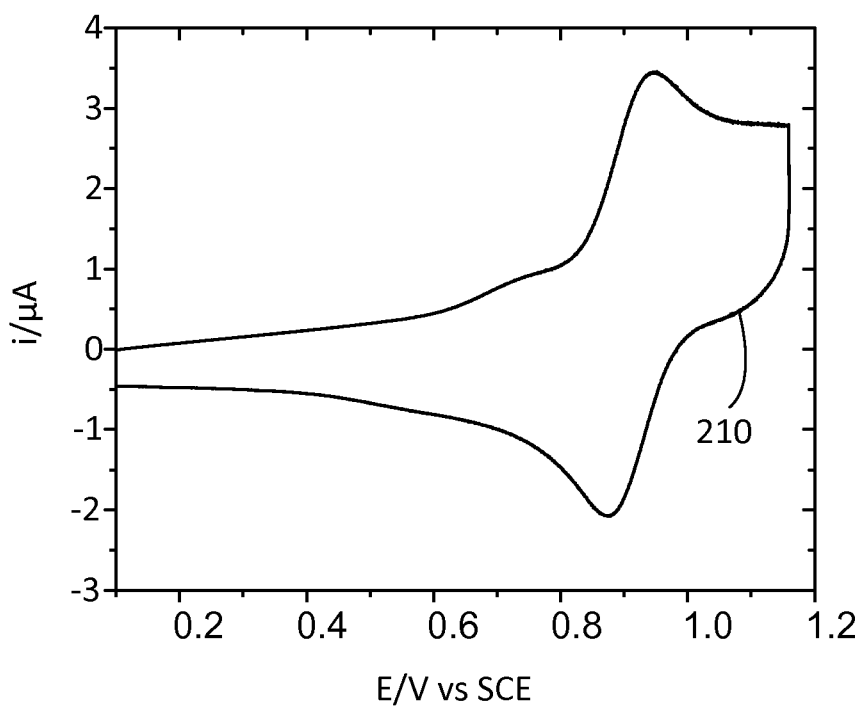
FIG. 2B depicts a cyclic voltamogram of Compound 1.

FIG. 2B shows a cyclic voltammogram for Compound 1 obtained as described above, with plot 210 corresponding to 35 mV/sec.

Compound 2.

6-(4-(2-(diphenylamino)naphthalen-6-yl)phenyl)-N,N-diphenylnaphthalen-2-amine, shown below, was synthesized in the following manner.

Compound 2

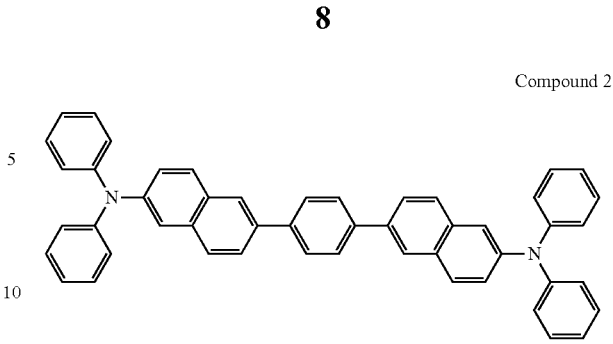

To a solution of 6-bromo-N,N-diphenylnaphthalen-2-amine (0.6415 g, 1.70 mmols) and 1,4-phenyldiboronic acid (0.144 g, 0.869 mmols) in toluene (10.5 mL) and ethanol (6.0 mL) was added a solution of sodium carbonate (0.87 g, 8 mmols) in water (8.0 mL). The solution was degassed with nitrogen, and then tetrakis(triphenylphosphine)palladium (0.165 g, 0.143 mmol) was added. The solution was again degassed with nitrogen and then heated to reflux in an oil bath at 83-85° C. and stirred for 4 hours. The reaction solution was then poured into ethyl acetate and water. A precipitate was filtered off, and the organic layer was dried over sodium sulfate, concentrated, and the crude product was chromatographed (0.5-1.0% ethyl acetate in hexanes, silica gel) to give the title compound (0.377 g, 66%) as a yellow, crystalline compound, m.p. 225-226° C.: ¹H NMR (400 MHz, CDCl₃) δ 8.04 (s, 2H), 7.82 (s, 4H), 7.77 (d, J=9.2 Hz, 2H), 7.74 (dd, J=8.8, 1.6 Hz, 2H), 7.68 (d, J=8.8 Hz, 2H), 7.46 (d, J=2.0 Hz, 2H), 7.33 (dd, J=8.8, 2.4 Hz, 2H), 7.27-7.32 (m, 8H), 7.17 (d, J=8.4 Hz, 8H), 7.07 (t, J=7.2 Hz, 2H); ¹³C NMR (100 MHz, CDCl₃) δ 147.7, 145.6, 139.8, 136.5, 133.6, 130.1, 129.3, 129.1, 127.5, 127.4, 125.7, 125.3, 124.7, 124.4, 123.0, 119.6; LCMS (M+H)⁺ Calc'd for $C_{50}H_{37}N_2$ 665.2957. found 665.2967.

Figure 3A:
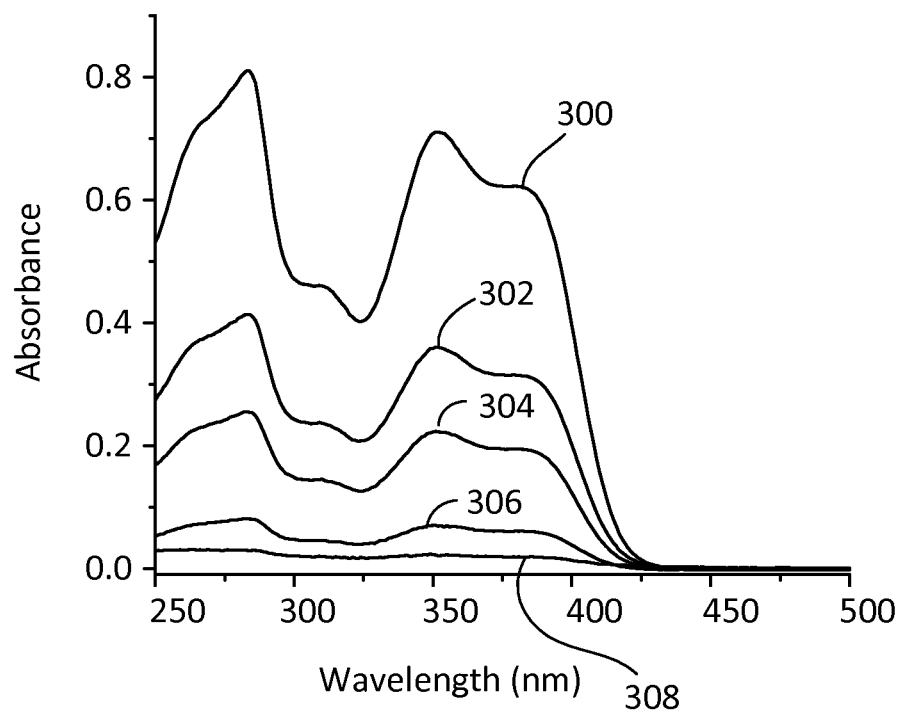
FIG. 3A depicts UV-vis spectra of 6-(4-(2-(diphenylamino)naphthalen-6-yl)phenyl)-N,N-diphenylnaphthalen-2-amine (Compound 2) at various concentrations.
Figure 3B:
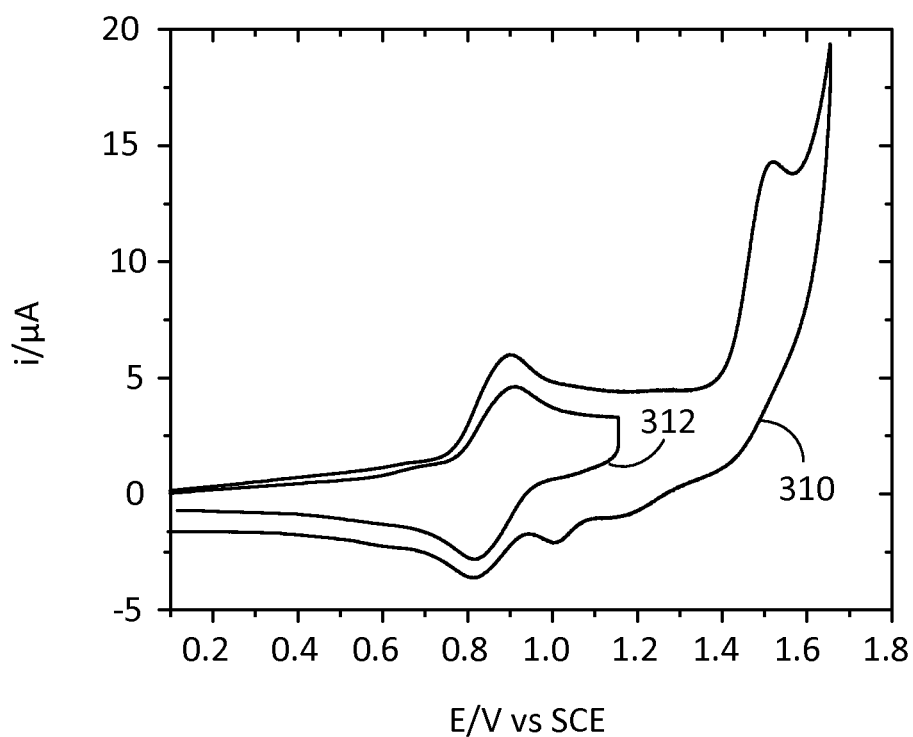
FIG. 3B depicts cyclic voltammograms of Compound 2.

FIG. 3A shows UV-vis spectra of Compound 2 synthesized as described above, with plots 300, 302, 304, 306, and 308 corresponding to concentrations of $1.25 \times 10^{-5}$ M, $6.26 \times 10^{-6}$ M, $3.75 \times 10^{-6}$ M, $1.25 \times 10^{-6}$ M, and $2.50 \times 10^{-7}$ M, respectively, in dichloromethane. The absorbance maximum a ($\lambda_{Max,Abs}$), emission maximum, a ($\lambda_{Max,Em}$), and extinction coefficient ($\epsilon$) are shown in Table I.

FIG. 3A shows cyclic voltammograms for Compound 2 obtained as described above, with plots 310 and 312 corresponding to 35 mV/sec. The small reduction "bump" at 1.0 volts vs. SCE in plot 310 is observed when Compound 2 is taken on an excursion to +1.7 volts vs. SCE. Plot 312 goes out to +1.18 volts, but the reduction bump on the return scan (around 1.0 volts) does not appear. This indicates that some "oxidized" species, generated on the high voltage excursion, may not be generated on a lower voltage excursion.

Compound 3.

6-(5-(2-(diphenylamino)naphthalen-6-yl)thiophen-2-yl)-N,N-diphenylnaphthalen-2-amine, shown below, was synthesized in the following manner.

Compound 3

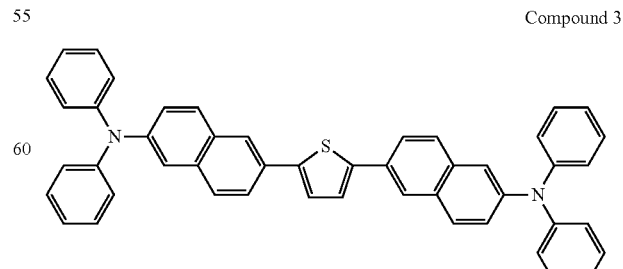

To a solution of 6-bromo-N,N-diphenylnaphthalen-2-amine (0.65 g, 1.70 mmols) and 2,5-thiophenediboronic acid (0.149 g, 0.87 mmols) in toluene (10.5 mL) and ethanol (6.0 mL) was added a solution of sodium carbonate (0.87 g, 8 mmols) in water (8.0 mL). The solution was degassed with nitrogen, and then tetrakis(triphenylphosphine)palladium (0.165 g, 0.143 mmol) was added. The solution was again degassed with nitrogen and then heated to reflux in an oil bath at 83-85° C. and stirred for 4 hours. The reaction solution was then poured into ethyl acetate and water. A precipitate was filtered off, and the organic layer was dried over sodium sulfate, concentrated, and the crude product was chromatographed (0.25-3.0% ethyl acetate in hexanes, silica gel) to give the title compound (0.091 g, 16%) as a yellow, crystalline compound: $^1$H NMR (400 MHz, CDCl$_3$) δ 8.00 (s, 2H), 7.72 (d, J=9.2 Hz, 2H), 7.70 (dd, J=8.8, 2.0 Hz, 2H), 7.59 (d, J=8.8 Hz, 2H), 7.31-7.41 (m, 4H), 7.26-7.31 (m, 10H), 7.17 (d, J=7.6 Hz, 8H), 7.07 (t, J=7.2 Hz, 4H); $^{13}$C NMR (100 MHz, CDCl$_3$) δ 147.6, 145.6, 143.6, 133.7, 130.2, 129.9, 129.3, 128.9, 127.4, 124.8, 124.5, 124.3, 124.0, 123.6, 123.1, 119.5; LCMS (M+H)$^+$ Calc'd for $C_{48}H_{35}N_2S$ 671.2521. found 671.2540.

Figure 4A:
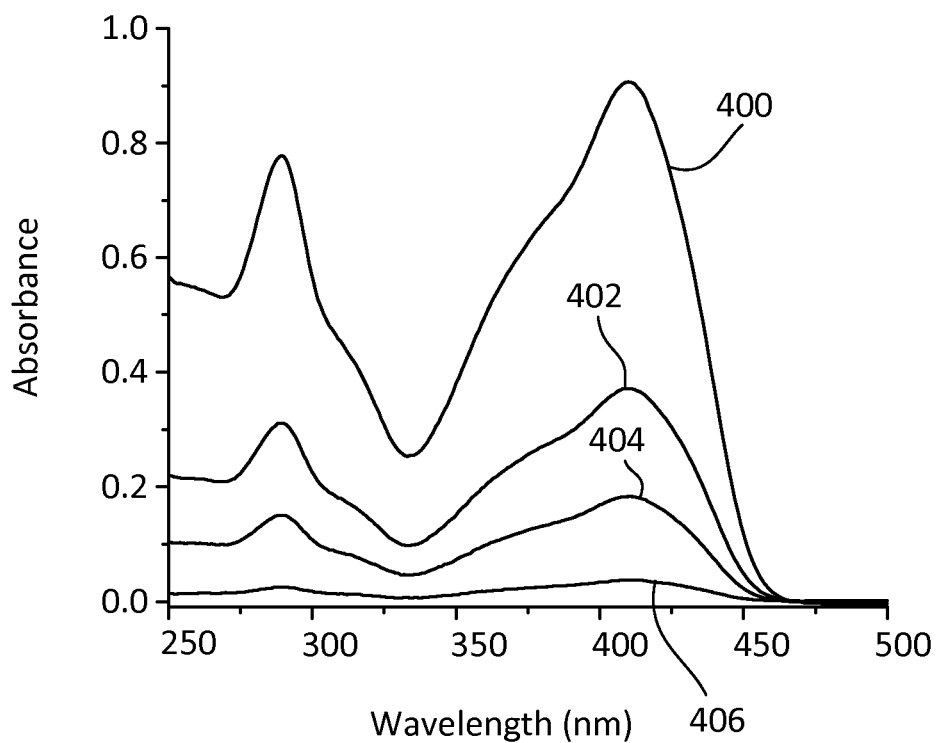
FIG. 4A depicts UV-vis spectra of 6-(5-(2-(diphenylamino)naphthalen-6-yl)thiophen-2-yl)-N,N-diphenylnaphthalen-2-amine (Compound 3) at various concentrations.

FIG. 4A shows UV-vis spectra of Compound 3 synthesized as described above, with plots 400, 402, 404, and 406 corresponding to concentrations of 1.49×10$^{-5}$ M, 5.96×10$^{-6}$ M, 2.98×10$^{-6}$ M, and 5.96×10$^{-7}$ M, respectively, in dichloromethane. The absorbance maximum ($\lambda_{Max,Abs}$), emission maximum ($\lambda_{Max,Abs}$), and extinction coefficient (ε) are shown in Table I.

Figure 4B:
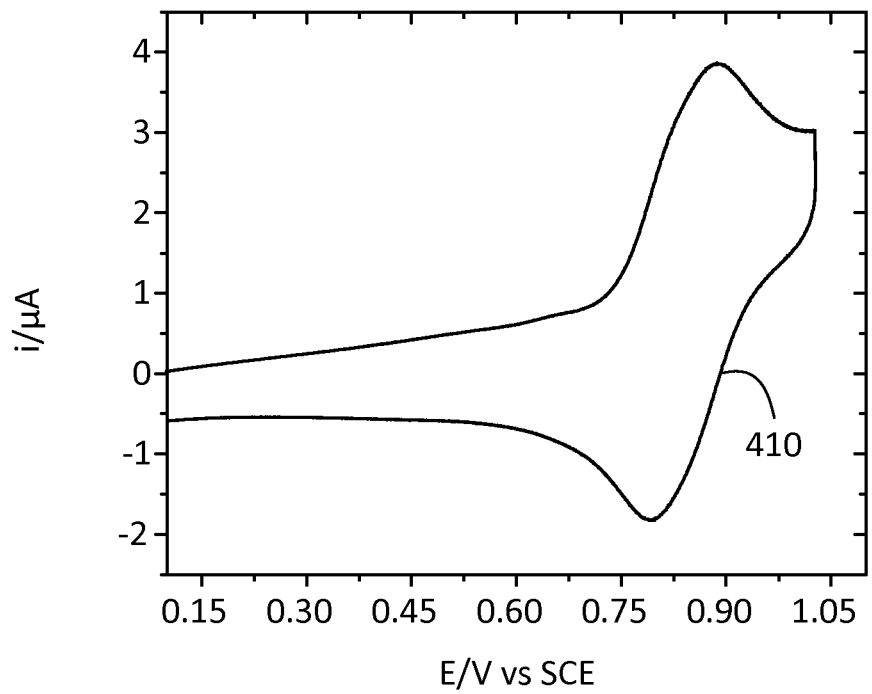
FIG. 4B depicts a cyclic voltammogram of Compound 3.

FIG. 4B shows a cyclic voltammogram for Compound 3 obtained as described above, with plot 410 corresponding to 35 mV/sec.

Figure 5A:
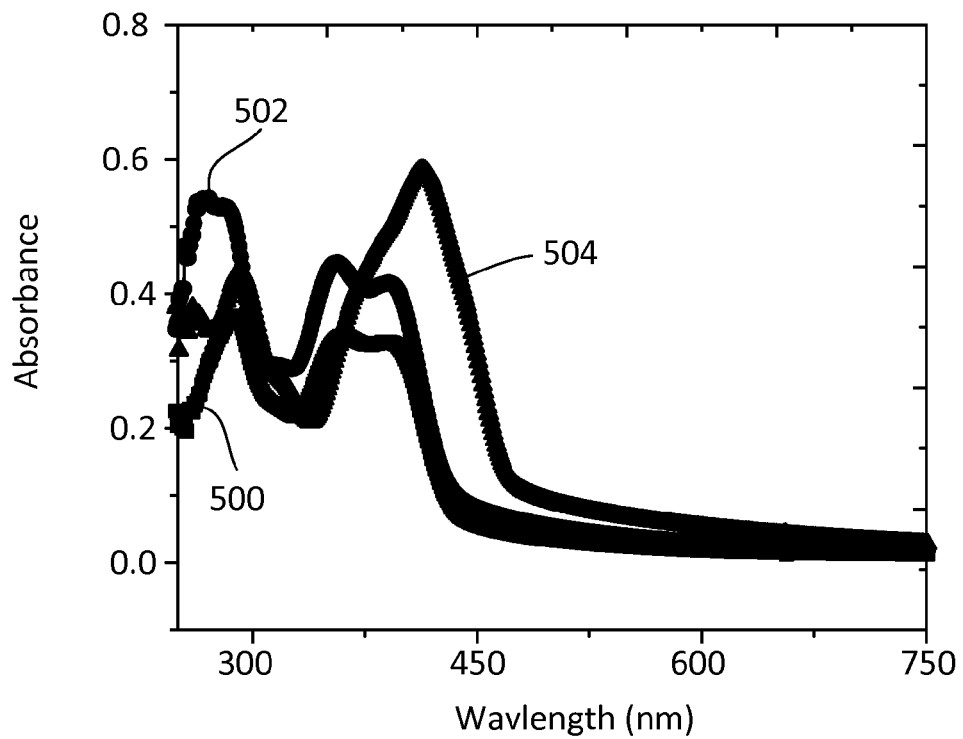
FIG. 5A shows absorbance spectra for thin films of Compounds 1-3.
Figure 5B:
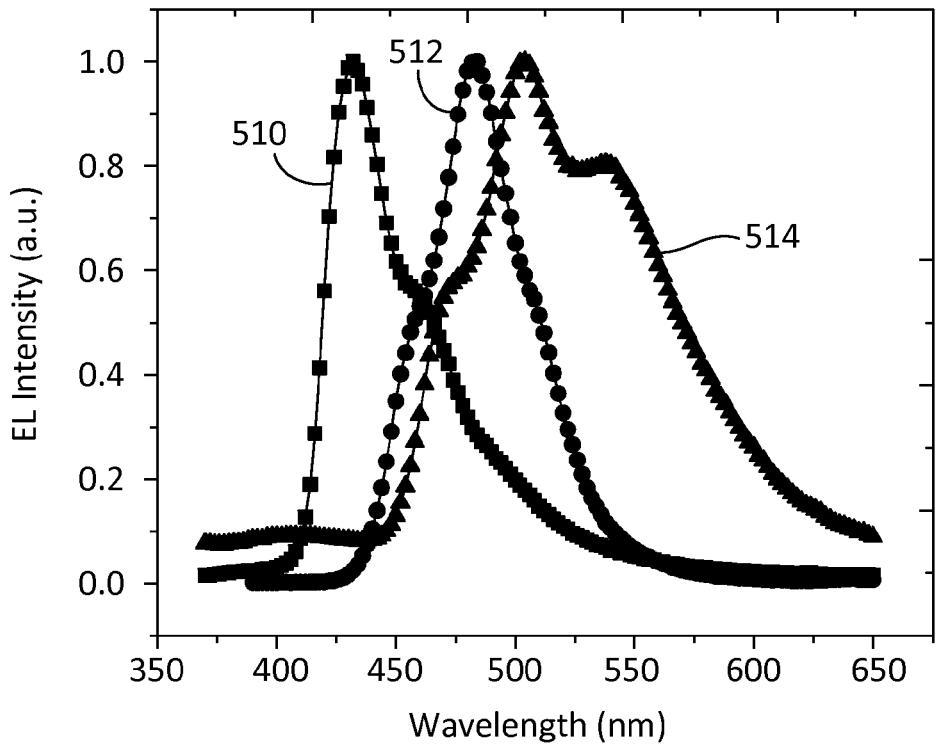
FIG. 5B shows electroluminescent intensity as a function of wavelength for thin films of Compounds 1-3.

Plots 500, 502, and 504 in FIG. 5A show absorbance versus wavelength for thin films of Compounds 1-3, respectively. Plots 510, 512, and 514 in FIG. 5B show electroluminescent intensity versus wavelength for the thin films of Compounds 1-3, respectively. Table II shows film thickness and maximum absorption and emission wavelengths for thin films of Compounds 1-3.

TABLE II

Properties of Compound 1-3 thin films.

|  | Film Thickness (nm) | $\lambda_{Max\,Abs}$ (nm) | $\lambda_{Max\,Em}$ (nm) |
| --- | --- | --- | --- |
| Compound 1 | 40 | 360 | 432 |
| Compound 2 | 50 | 357 | 484 |
| Compound 3 | 58 | 414 | 504 |

OLEDs including Compounds 1-3 and an OLED with NPD were prepared as follows. Patterned ITO was cleaned with Alconox, acetone, AZ 1512 photoresist, and acetone followed by ultraviolet (UV) ozone treatment. All devices were fabricated in a Kurt J. Lesker vacuum thermal evaporation chamber. After the deposition of organic layers, the substrates were taken out, shadow masks were placed on and the substrates were then loaded into the chamber again to complete the cathode LiF (1 nm)/Al (100 nm). The electrical and optical characteristics of the devices were measured with a Keithly 2400 source/meter/2000 multimeter coupled to a Newport 1835-C optical meter, equipped with a UV 818 Si photo detector in ambient atmosphere and at room temperature. Light was collected from the front face of the substrate only. Electroluminescence spectra were measured by a PTI QuantaMaster model C-60SE spectrophotometer, equipped with a 928 PMT detector and corrected for detector response.

Figure 6A:
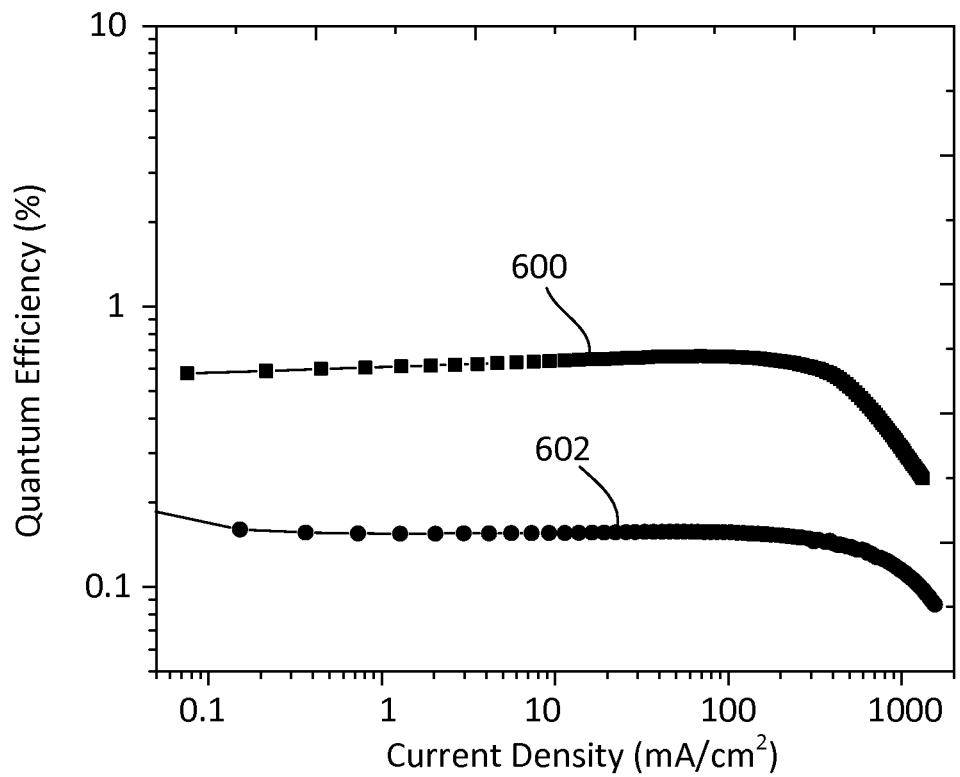
FIGS. 6A-6D show quantum efficiency versus current density, brightness versus voltage, current density versus voltage, and electroluminescent intensity versus wavelength, respectively, for an OLED including Compound 1.
Figure 6B:
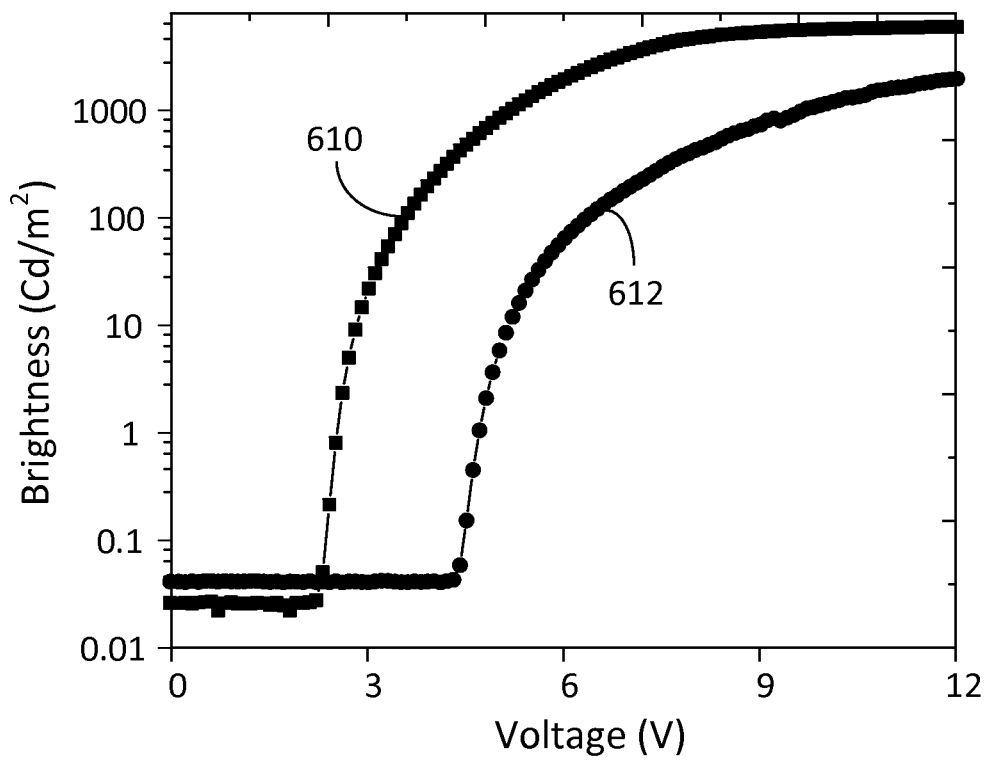
Figure 6C:
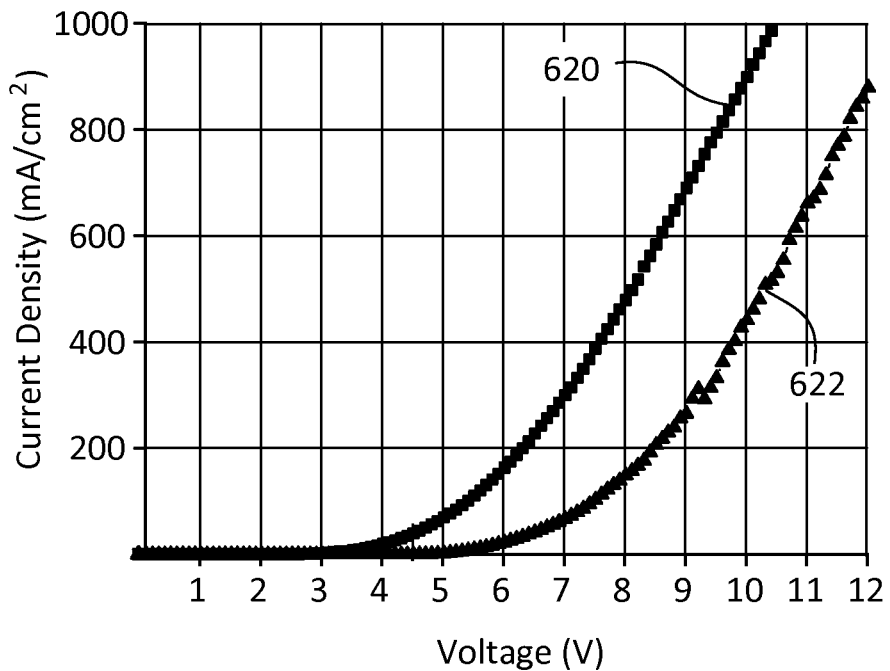
Figure 6D:
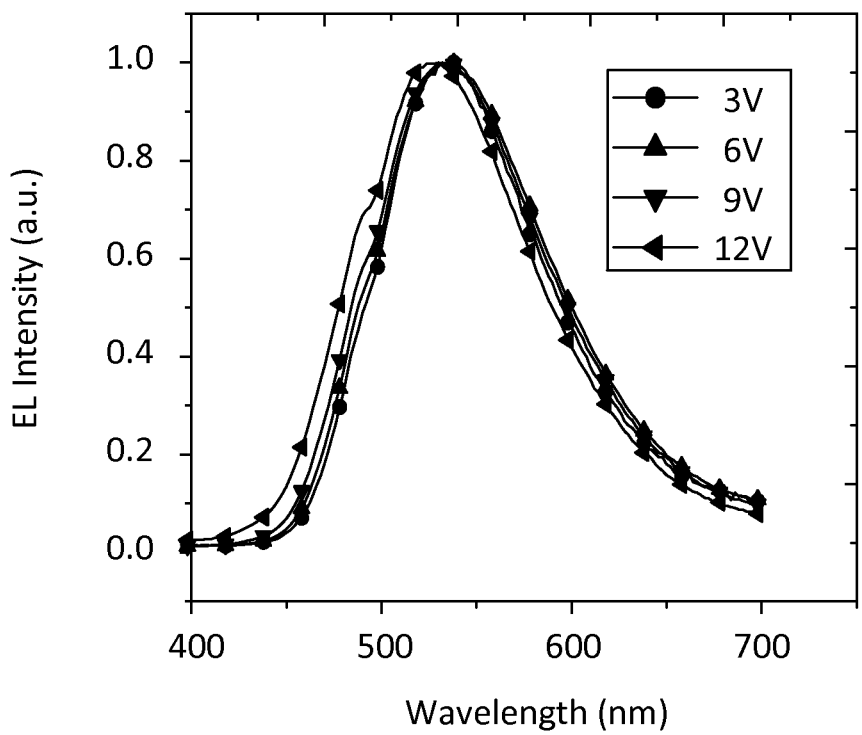

Plots 600 and 602 in FIG. 6A show quantum efficiency versus current density for the comparative OLED and an OLED including Compound 1, respectively. Plots 610 and 612 in FIG. 6B show brightness versus voltage for the comparative OLED and the OLED including Compound 1, respectively. Plots 620 and 622 in FIG. 6C show current density versus voltage for the comparative OLED and the OLED including Compound 1, respectively. FIG. 6D shows electroluminescent intensity for the OLED including Compound 1 at 3 V, 6 V, 9 V, and 12 V.

Figure 7A:
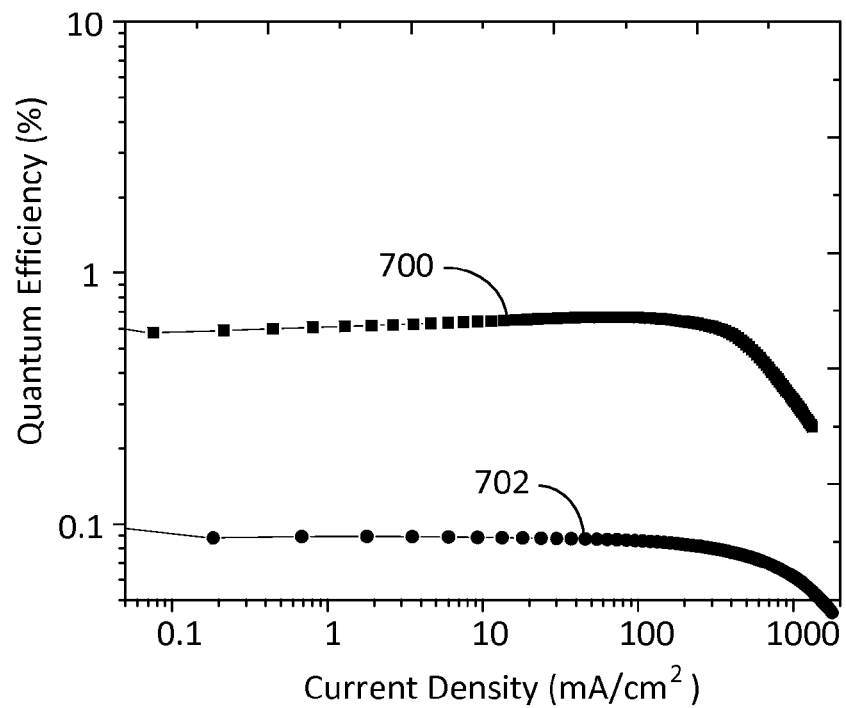
FIGS. 7A-7D show quantum efficiency versus current density, brightness versus voltage, current density versus voltage, and electroluminescent intensity versus wavelength, respectively, for an OLED including Compound 2.
Figure 7B:
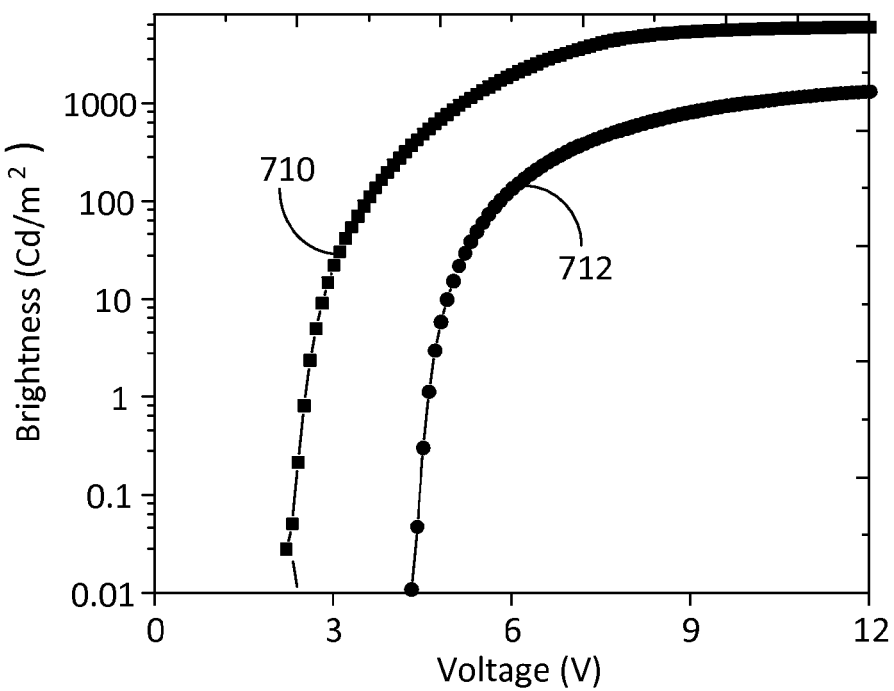
Figure 7C:
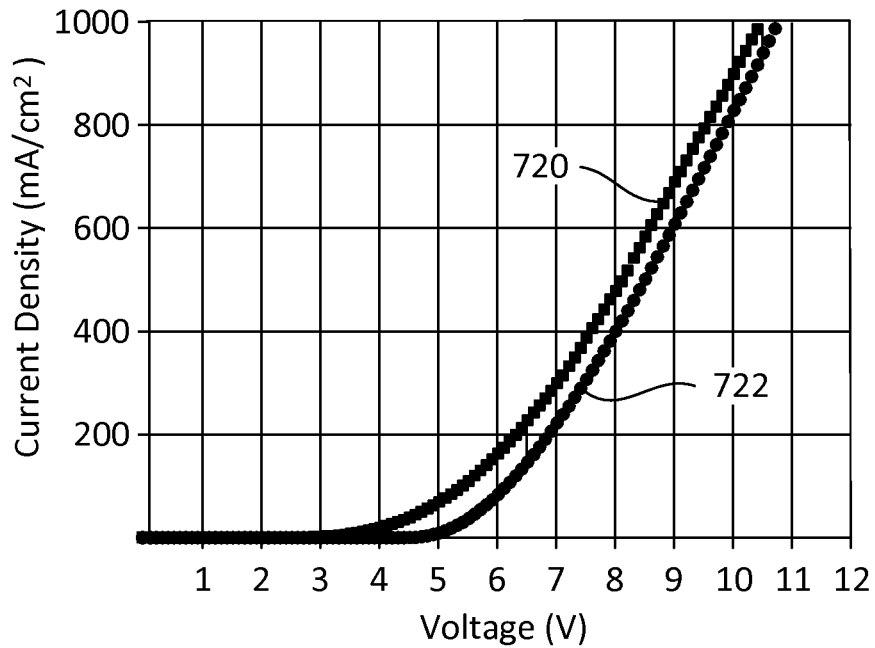
Figure 7D:
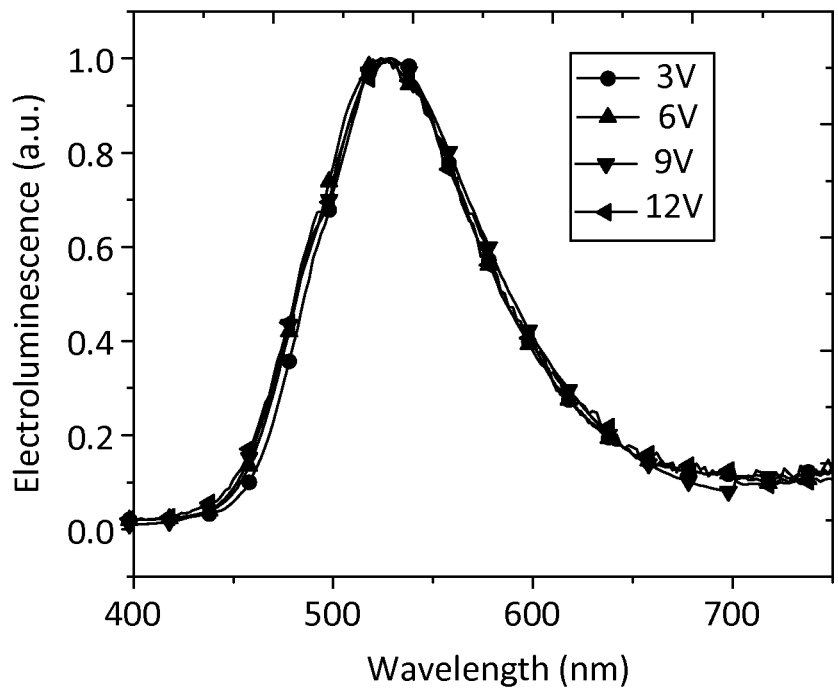

Plots 700 and 702 in FIG. 7A show quantum efficiency versus current density for the comparative OLED and an OLED including Compound 2, respectively. Plots 710 and 712 in FIG. 7B show brightness versus voltage for the comparative OLED and the OLED including Compound 2, respectively. Plots 720 and 722 in FIG. 7C show current density versus voltage for the comparative OLED and the OLED including Compound 2, respectively. FIG. 7D shows electroluminescent intensity for the OLED including Compound 2 at 3 V, 6 V, 9 V, and 12 V.

Figure 8A:
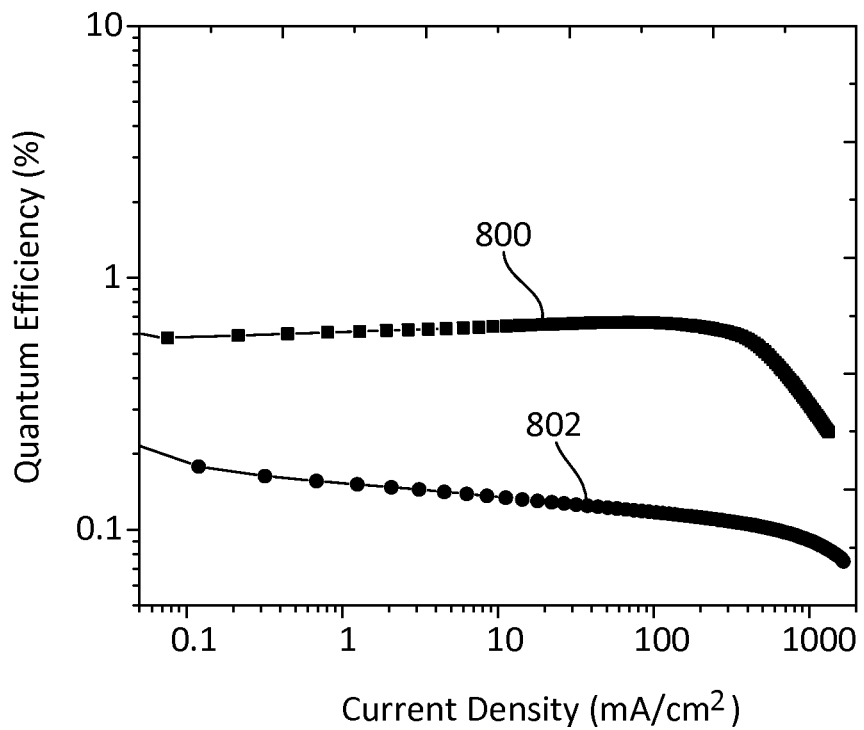
FIGS. 8A-8D show quantum efficiency versus current density, brightness versus voltage, current density versus voltage, and electroluminescent intensity versus wavelength, respectively, for an OLED including Compound 3.
Figure 8B:
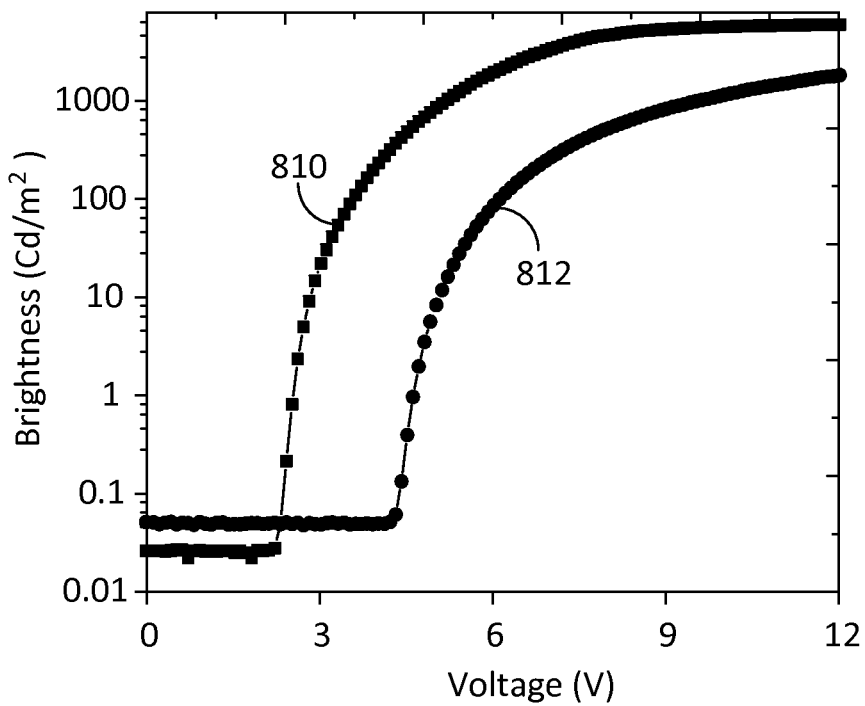
Figure 8C:
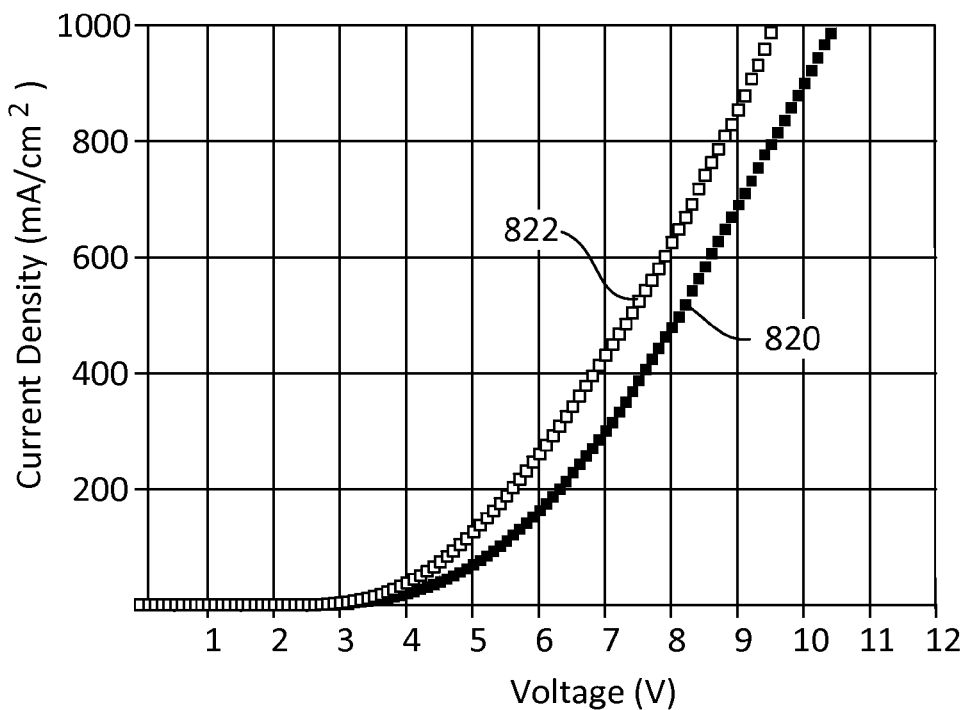
Figure 8D:
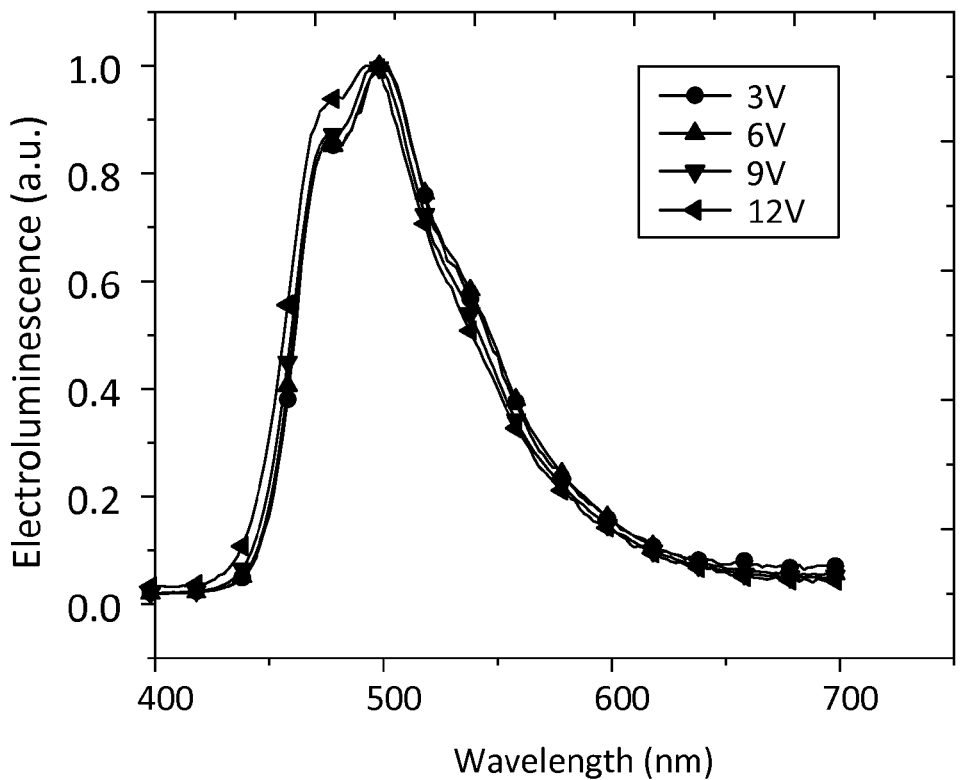

Plots 800 and 802 in FIG. 8A show quantum efficiency versus current density for the comparative OLED and an OLED including Compound 3, respectively. Plots 810 and 812 in FIG. 8B show brightness versus voltage for the comparative OLED and the OLED including Compound 3, respectively. Plots 820 and 822 in FIG. 8C show current density versus voltage for the comparative OLED and the OLED including Compound 3, respectively. FIG. 8D shows electroluminescent intensity for the OLED including Compound 3 at 3 V, 6 V, 9 V, and 12 V.

Table III shows hole transport layer (HTL) and electron transport layer (ETL-Alq$_3$ or tris(8-hydroxyquinolinato)aluminium) composition for the comparative OLED and OLEDs including Compounds 1-3 described herein, as well as $V_{on}$, $L_{max}$, and external quantum efficiency ($EQE_{max}$). The HTL and ETL were 40 nm thick.

TABLE III

Properties of Comparative and Compound 1-3 OLEDs.

| OLED | HTL | ETL | $V_{on}$ (V) | $L_{max}$ (cd/m$^2$) | $EQE_{max}$ (%) |
| --- | --- | --- | --- | --- | --- |
| Comparative | NPD | Alq$_3$ | 2.6 | 5995 | 0.67 |
| Compound 1 | Compound 1 | Alq$_3$ | 4.4 | 2504 | 0.16 |
| Compound 2 | Compound 2 | Alq$_3$ | 4.6 | 1451 | 0.09 |
| Compound 3 | Compound 3 | Alq$_3$ | 2.6 | 2293 | 0.14 |

Figure 9A:
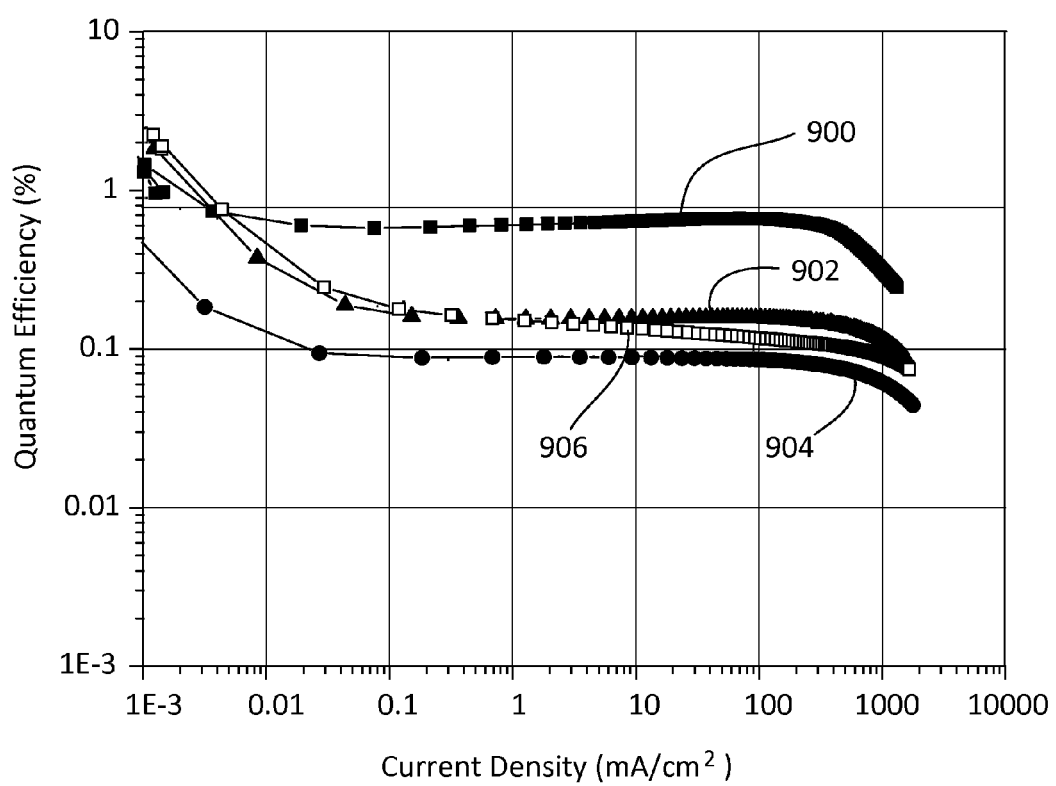
FIGS. 9A-9C show a comparison of quantum efficiency versus current density, brightness versus voltage, and current density versus voltage for OLEDs including Compounds 1-3 and a comparative OLED.
Figure 9B:
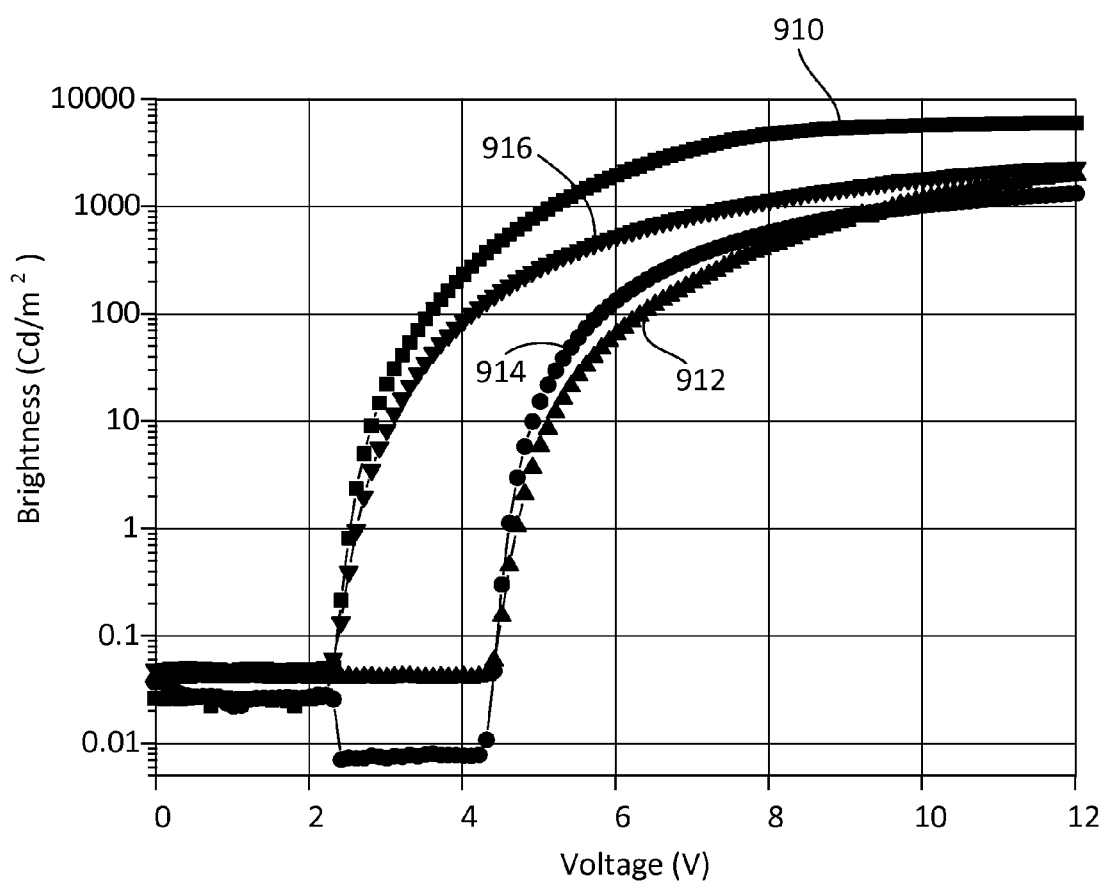
Figure 9C:
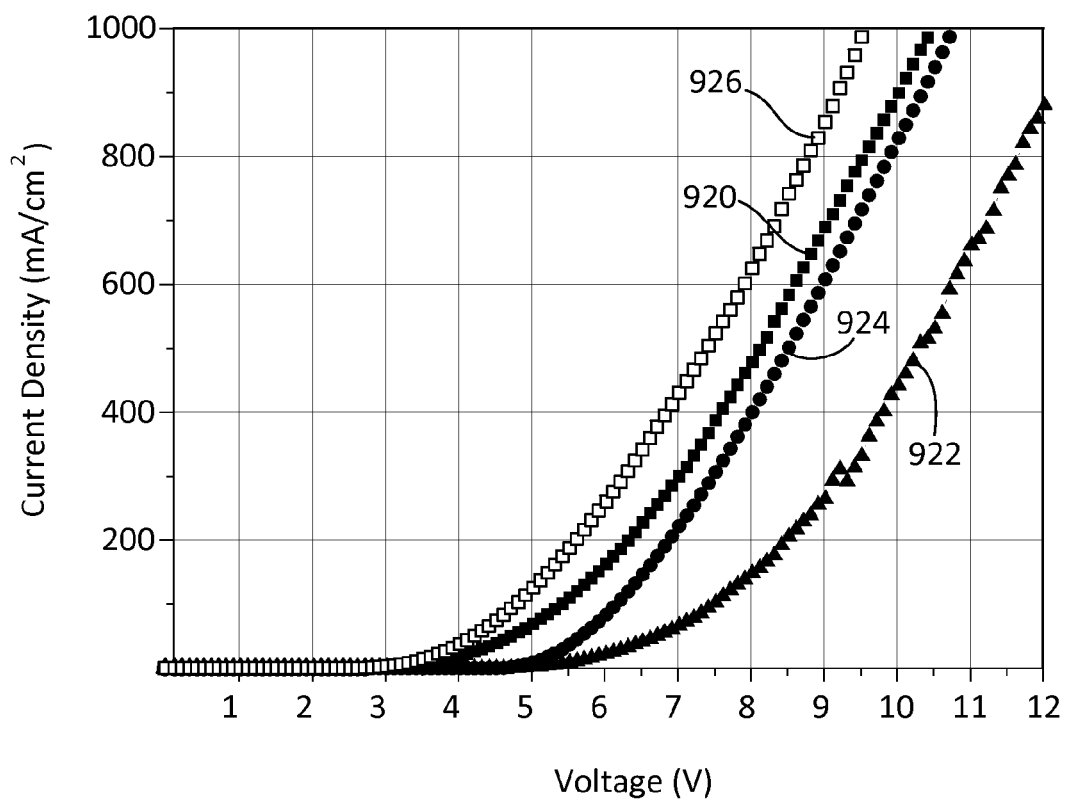

Plots 900, 902, 904, and 906 in FIG. 9A show quantum efficiency versus current density for the comparative OLED and OLEDs including Compounds 1-3, respectively. Plots 910, 912, 914, and 916 in FIG. 9B show brightness versus voltage for the comparative OLED and OLEDs including Compounds 1-3, respectively. Plots 920, 922, 924, and 926 in FIG. 9C show current density versus voltage for the comparative OLED and OLEDs including Compounds 1-3, respectively.

OLEDs described herein can be used in devices such as televisions, laptop computers, computer monitors, personal digital assistants, mobile phones, portable media players, watches, test devices, advertising displays, information displays, indication displays, and large-area light-emitting elements for general illumination in the wavelength range between 400 nm and 700 nm (e.g., 450 nm to 650 nm, 500 nm to 600 nm).

A number of embodiments of the invention have been described. Nevertheless, it will be understood that various modifications may be made without departing from the spirit and scope of the invention. Accordingly, other embodiments are within the scope of the following claims. Further modifications and alternative embodiments of various aspects will be apparent to those skilled in the art in view of this description. Accordingly, this description is to be construed as illustrative only. It is to be understood that the forms shown and described herein are to be taken as examples of embodiments. Elements and materials may be substituted for those illustrated and described herein, parts and processes may be reversed, and certain features may be utilized independently, all as would be apparent to one skilled in the art after having the benefit of this description. Changes may be made in the elements described herein without departing from the spirit and scope as described in the following claims. All cited patents, patent applications and references are incorporated by reference in their entireties for all purposes.

What is claimed is:

1. A compound having the structural formula $S_2R$, wherein S is:

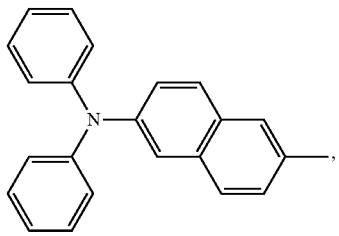 [SMILES: Cc1ccc2cc(N(c3ccccc3)c3ccccc3)ccc2c1]

and $S_2R$ has the skeleton:

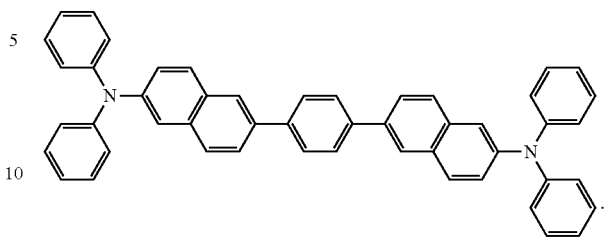

2. A compound having the structural formula $S_2R$, wherein S is:

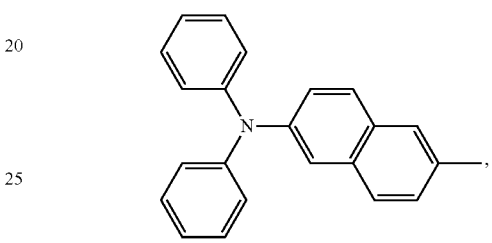

and $S_2R$ has the skeleton:

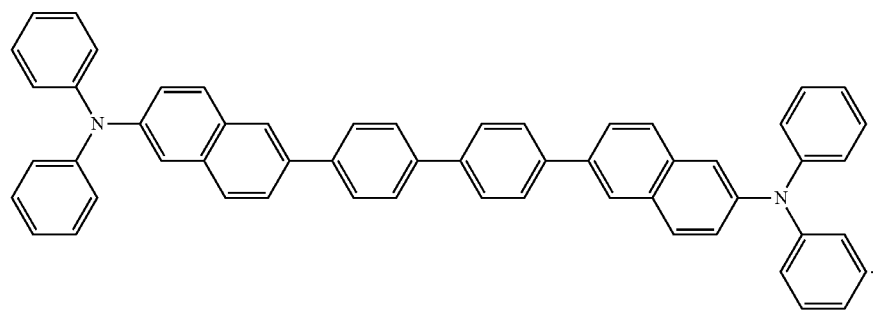 [SMILES: c1ccc(N(c2ccccc2)c2ccc3cc(-c4ccc(-c5ccc(-c6ccc7cc(N(c8ccccc8)c8ccccc8)ccc7c6)cc5)cc4)ccc3c2)cc1]

3. An organic light-emitting diode comprising the compound of claim 1.

4. A device comprising the organic light-emitting diode of claim 3.

5. The device of claim 4, wherein the device is selected from the group consisting of televisions, laptop computers, computer monitors, personal digital assistants, mobile phones, portable media players, watches, test devices, advertising displays, information displays, indication displays, and large-area light-emitting elements for general illumination.

6. An organic light-emitting diode comprising the compound of claim 2.

7. A device comprising the organic light-emitting diode of claim 6.

8. The device of claim 7, wherein the device is selected from the group consisting of televisions, laptop computers, computer monitors, personal digital assistants, mobile phones, portable media players, watches, test devices, advertising displays, information displays, indication displays, and large-area light-emitting elements for general illumination.

* * * * *